US011944132B2

(12) United States Patent
Hettich

(10) Patent No.: US 11,944,132 B2
(45) Date of Patent: Apr. 2, 2024

(54) ADJUSTABLE ORTHOSTATIC INTOLERANCE SYSTEM AND GARMENT

(71) Applicant: BSN Medical Inc., Charlotte, NC (US)

(72) Inventor: Mary Ann Hettich, Matthews, NC (US)

(73) Assignee: BSN MEDICAL, INC., Charlotte, NC (US)

( * ) Notice: Subject to any disclaimer, the term of this patent is extended or adjusted under 35 U.S.C. 154(b) by 452 days.

(21) Appl. No.: 16/661,754

(22) Filed: Oct. 23, 2019

(65) Prior Publication Data

US 2020/0054513 A1 Feb. 20, 2020

Related U.S. Application Data

(63) Continuation of application No. 14/220,339, filed on Mar. 20, 2014, now Pat. No. 10,478,366, which is a continuation of application No. 13/075,739, filed on Mar. 30, 2011, now abandoned.

(60) Provisional application No. 61/319,084, filed on Mar. 30, 2010.

(51) Int. Cl.
*A41B 11/14* (2006.01)
*A61F 13/08* (2006.01)
*A61F 13/14* (2006.01)
*A61H 1/00* (2006.01)

(52) U.S. Cl.
CPC .............. *A41B 11/14* (2013.01); *A61F 13/08* (2013.01); *A61F 13/148* (2013.01); *A61H 1/008* (2013.01); *A41B 2400/32* (2013.01)

(58) Field of Classification Search
CPC ........ A61F 13/08; A61F 13/06; A61F 13/143; A61F 5/02; A61F 5/03; D04B 1/265; D04B 1/24; D10B 2501/021; A41B 11/14; A41B 11/143; A41B 11/146; A41B 11/08
USPC ........ 602/60, 62, 53, 75–76; 2/69, 227, 228; D2/714; 66/171; 601/84
See application file for complete search history.

(56) References Cited

U.S. PATENT DOCUMENTS

| 2,370,754 A | 3/1945 | Roseman |
| 4,368,549 A | 1/1983 | White |
| 5,315,716 A | 5/1994 | Baum |

(Continued)

FOREIGN PATENT DOCUMENTS

| FR | 2915851 A1 * | 11/2008 | ......... A41D 13/0015 |
| FR | 2915851 B1 | 11/2008 | |
| FR | 2915851 | 2/2013 | |

OTHER PUBLICATIONS (aesthetic insiders.PDF) Loo, Lynette: "Comfortweave vs Powernet: A Quick Guide". accessed from aestheticinsders.com on Jan. 14, 2022 (Year: 2019).*

(Continued)

*Primary Examiner* — Caitlin A Carreiro
(74) *Attorney, Agent, or Firm* — Shumaker, Loop & Kendrick, LLP; S. Alexander Long, Jr.

(57) ABSTRACT

An adjustable orthostatic intolerance garment formed of a knitted spandex powernet construction in order to provide compression when on the leg, and including legs and a torso portion that extends upwardly into the abdominal area below the pectoral muscles; and a respective pair of elongate panels that are retained in place by attaching elements, and that are introduced into or removed from the garment to increase or reduce compression on the wearer's body as desired.

22 Claims, 8 Drawing Sheets

(56) References Cited

U.S. PATENT DOCUMENTS

| | | | | |
|---|---|---|---|---|
| 5,653,244 | A * | 8/1997 | Shaw | A61F 13/085 |
| | | | | 128/882 |
| 6,296,618 | B1 * | 10/2001 | Gaber | A61F 13/143 |
| | | | | 602/61 |
| 2005/0034205 | A1 * | 2/2005 | Green | A63B 21/0004 |
| | | | | 2/69 |
| 2006/0189913 | A1 * | 8/2006 | Winkler | A61F 13/08 |
| | | | | 602/61 |
| 2010/0170026 | A1 | 7/2010 | Jeffords | |
| 2012/0078147 | A1 * | 3/2012 | Ogulnick | A61F 13/143 |
| | | | | 602/2 |

OTHER PUBLICATIONS

Loo, Lynette: "Comfortweave vs Powernet: A Quick Guide"—aesthetic insiders.PDF (Year: 2019).*
From Loo, Lynette: "Comfortweave vs Powernet: A Quick Guide"⇒aesthetic insiders.PDF (Year: 2019).*
Denier of Spandex Yarns—Google Search. PDF (Year: 2022).*
Machine translation of FR2915851 (Year: 2008).*

* cited by examiner

ADJUSTABLE ORTHOSTATIC INTOLERANCE SYSTEM AND GARMENT

CROSS-REFERENCE TO RELATED APPLICATIONS

This application is a continuation of co-pending U.S. application Ser. No. 14/220,339, filed on Mar. 20, 2014, claiming priority to U.S. application Ser. No. 13/075,739, filed on Mar. 30, 2011, which claims priority to U.S. Provisional Application No. 61/319,084, filed on Mar. 30, 2010, the entire contents of each are hereby incorporated by reference in the entirety.

TECHNICAL FIELD AND BACKGROUND OF THE INVENTION

During extended periods of exposure to a gravity free environment such as experienced by astronauts, the body's fluids redistribute in response to the weightless environment. This fluid change triggers responses in the autonomic nervous and cardiovascular systems which, when coupled with low humidity conditions in space vehicles, results in progressive fluid volume loss and symptoms associated with dehydration. This is called "orthostatic intolerance." Attempts have been made to resolve these problems upon return to Earth by applying various types of compression garments to the astronauts upon return to Earth. However, prior efforts have been limited by variation in the amount of fluid volume loss from astronaut to astronaut, so that in some cases the compression garments were so loose that they did not function adequately.

To counter the effects of orthostatic intolerance upon return to earth's gravitational force, it has been determined that it is desirable to use a "gradient compression garment," and to maintain a desired compression profile even with dimensional changes in the body. The primary areas of concern are the upper thigh and abdomen.

A second need is to provide a means of gradually returning the astronauts back to normal gravitational exposure. To accomplish this, it is proposed to provide a means in which the compression level can be incrementally reduced.

There are multiple advantages that the system described below provides over current garments and garment system. First, the system may serve to adjust the compressive force (fabric tension) over areas of the body most susceptible to volume loss during extended exposure to a non-gravity environment. Second, the system may provide precise adjustments of the garment to ensure a continuous applied pressure gradient, being highest at the ankle and decreasing proximally. Third, the system may permit gradually reintroducing the astronaut to normal gravitational forces upon return to earth after extended stays in weightlessness. Fourth, the system may apply compression to the wearer promptly after re-entry into a gravity environment without the need for an air supply or electrical power for pumps or other pressure-inducing means.

SUMMARY OF THE INVENTION

Therefore, a system that includes one, two or three inter-related garments and hosiery products has been developed that improves adjustment of astronauts to the effect of gravity on the fluid retention and placement in the body.

A 3-piece system consisting of two thigh length supports (one for each leg) of a non-standard compression profile (~55 mmHg at the ankle and gradually decreasing to ~23 mmHg at the thigh), and a garment that extends above the waist to just below the pectorals and approximately to mid-thigh on both legs. The garment includes a tapered panel inserted on either side that extends along the entire length of the body and ends at the thigh circumference. Separating zippers are attached longitudinally on either side of the panel to enable separation and removal of the panel section and reformation of the brief at a reduced circumference.

The degree of taper and the width of the panel are configured such as to provide ±2 mmHg to a body that may experience up to 4 cm of circumferential change. The garment may include multiple tapered inserts, or panels, that are adjacent to one another on either or both sides of the body. Thigh extensions are designed to be worn over the upper portion of the thigh length support described above, and the combination of which maintains a gradient compression profile.

One embodiment of the garment includes a double wall abdominal panel that extends from the pubis to the top of the support. The double panel is made from the same body fabric and is intended to provide additional extension resistance and support over the abdominal fluid reservoir. In one embodiment, elastic bands are attached to the lower ends that form around the thigh and at the top of the garment. Tabs are attached to affect continuity of the elastic loops after zipper closure.

Thigh length supports are also adapted to include enclosed zippers that are inserted on the medial aspect of the garment extending distally from the base of the gastrocnemius to the medial malleolus.

One embodiment of the invention is a 3-piece system having two thigh length supports (one for each leg) of a non-standard compression profile (~55 mmHg at the ankle and gradually decreasing to ~23 mmHg at the thigh), and a garment that extends above the waist to just below the pectorals and approximately to mid-thigh on both legs.

An adjustable means on either side of the garment extends along the entire length of the body and ends at the thigh circumference. The adjustable mechanism(s) are attached to the elastic body fabric in such a manner as to pull the fabric to a higher tension and the brief to a reduced circumference. The degree of width adjustment/tightening of the body fabric is configured such as to provide ±2 mmHg to a body that may experience up to 4 cm of circumferential change.

A garment is also proposed in which the adjustable mechanism is interlacing and a means for discretely cinching them, such as by the BOA Lacing system that enables lacings to be tightened or loosened in discrete increments by rotating a knob in the desired direction.

Alternatively, the adjustable mechanism may be a series of hooks and eyes.

Another alternative construction is a garment in which the adjustable mechanism is hook and loop type fasteners upon which specific gradations or landmarks have been applied to identify specific degrees of tightening.

In a further alternative construction, the adjustable mechanism is a series of full length separating zippers spaced in defined increments.

In one embodiment, a garment includes thigh extensions designed to be worn over the upper portion of the thigh length support, the combination of which maintains a gradient compression profile.

A further embodiment includes elastic bands attached to the lower ends that form around the thigh and at the top of the garment. Tabs are attached to affect continuity of the elastic loops after zipper closure.

A system of compression garments provides a non-standard compression profile (~55 mmHg at the ankle and gradually decreasing to ~23 mmHg at the thigh), and a garment that extends above the waist to just below the pectorals and approximately to mid-thigh on both legs.

One embodiment includes a knee high "liner" sock providing ~15 mmHg at the ankle and an open-toe thigh length over stocking that provides ~40 mmHg at the ankle.

BRIEF DESCRIPTION OF THE DRAWINGS

Some of the objects of the invention have been set forth above. Other_objects and advantages of the invention will appear as the description of the invention _proceeds when taken in conjunction with the following drawings, in which.

DESCRIPTION OF THE PREFERRED EMBODIMENTS AND BEST MODE

Figure 1:
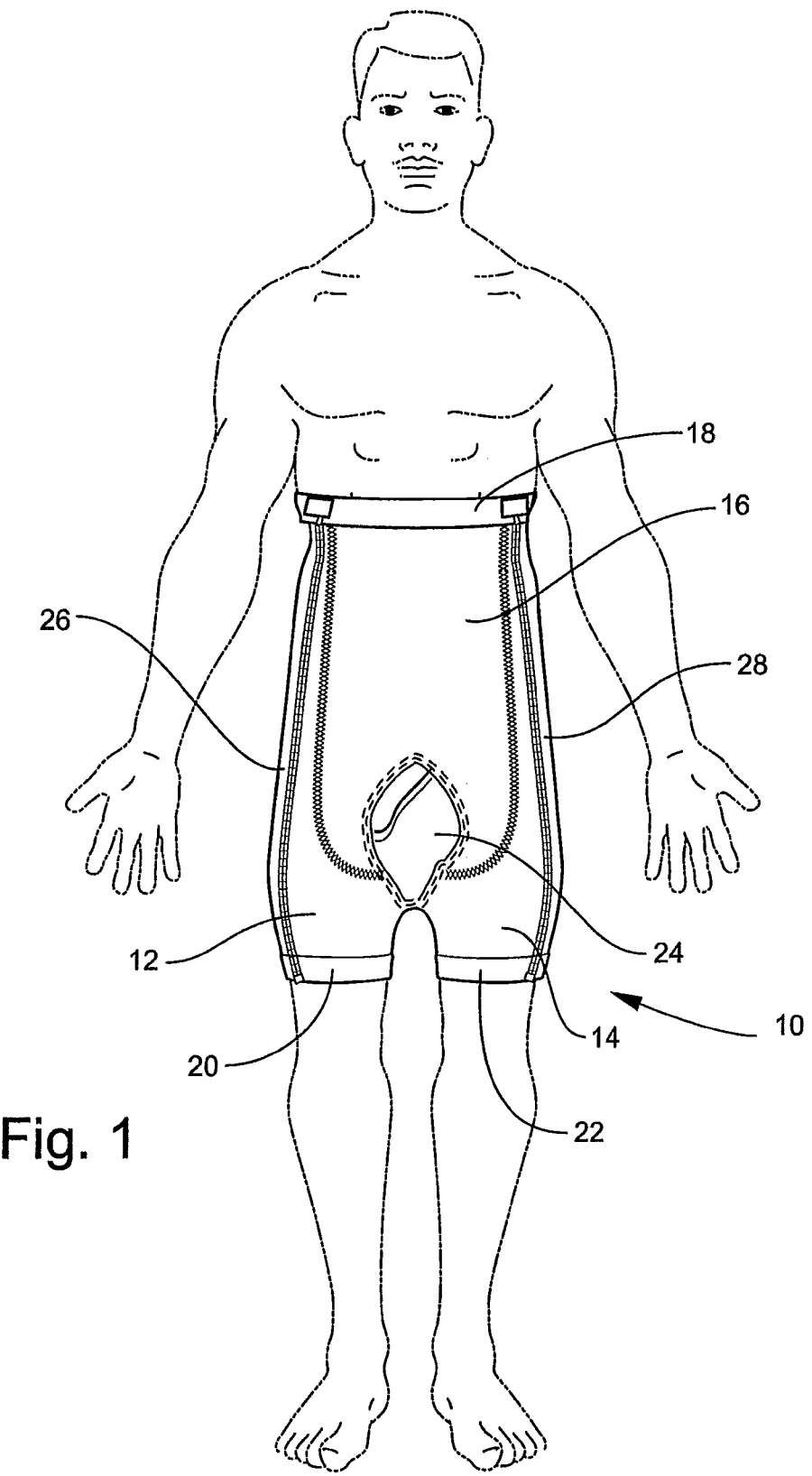
FIG. 1 is an overall view of an adjustable orthostatic intolerance garment_system according to one embodiment of the invention in position on a human body.

Referring now specifically to the drawings, an adjustable orthostatic intolerance garment system according to one embodiment of the invention in position on a human body is shown generally in FIG. 1, at reference numeral 10.

Figure 2:
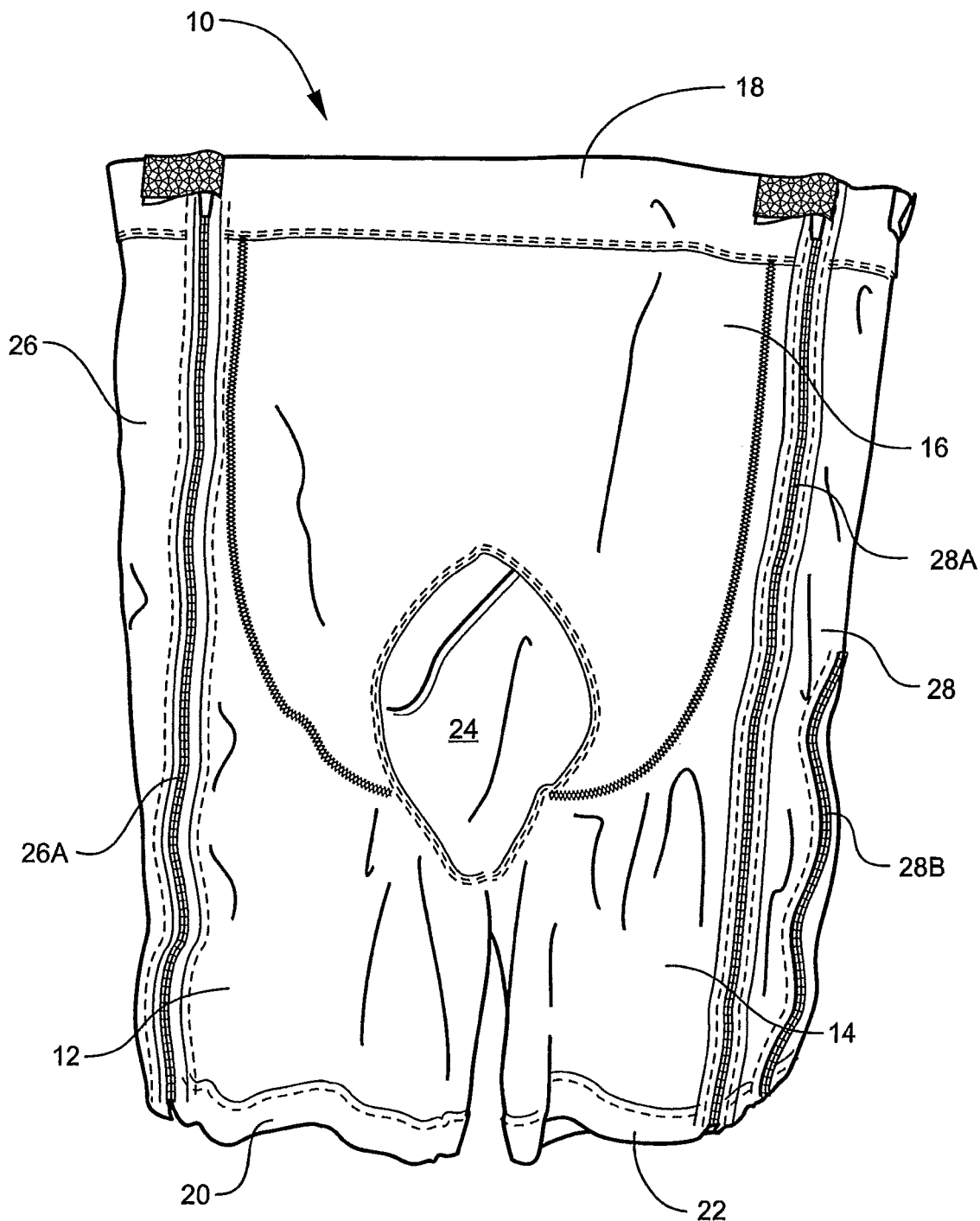
FIG. 2 illustrates an embodiment of a body an adjustable orthostatic_intolerance garment according to one embodiment of the invention.
Figure 3:
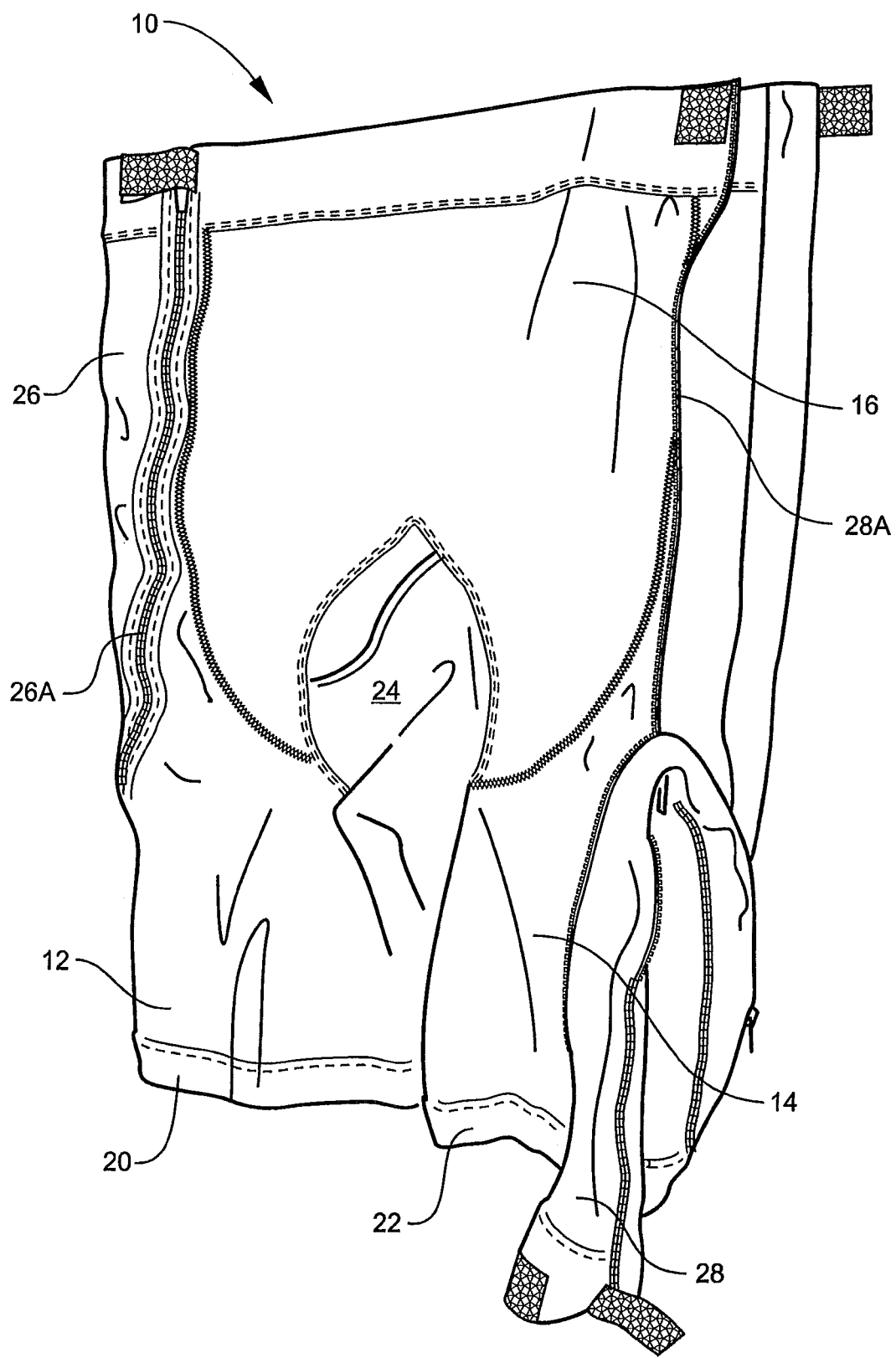
FIG. 3 illustrates another embodiment of a body an adjustable orthostatic_intolerance garment according to one embodiment of the invention.

As is shown more specifically in FIGS. 2 and 3, the garment 10 as generally illustrated in FIG. 1 is formed of a knitted spandex powernet construction using either 840 or 1120 Denier spandex yarns in order to provide pressure of about 55 mmHg when in place on the leg. The garment 10 includes legs 12, 14, and a torso portion 16 that extends upwardly into the abdominal area below the pectoral muscles. The garment 10 includes an elastic band 18 at the upper end and elastic bands 20, 22 at each leg bottom to prevent the legs 12, 14 from riding up the thigh. A fly 24 for use when worn by a male, or a flap (not shown) for use when worn by a female, is provided. In the particular embodiment shown in FIGS. 2 and 3, and best shown in FIG. 3, legs 12, 14 include a respective pair of elongate tapered panels 26, 28 that are retained in place by zippers, as is best shown in FIG. 3, where the panel 28 is shown partially unzipped from zippers 28A, 28B. Panel 26 is retained on the garment 10 and removed by complementary zippers 26A, and 26B (26B not shown).

When initially donned by a wearer suffering from fluid loss, the garment 10 is used without the panels 26, 28, and the zippers 26A, 26B and 28A, 28B are zipped together. As fluid is replaced in the wearer, the wearer may be given additional room with essentially the same or similar compression gradient by inserting the panels 26, 28 into the garment 10. This is accomplished by unzipping the zippers 26A, 26B and 28A, 28B, and attaching the panel to the garment with complementary zipper components carried by the panel.

Figure 4:
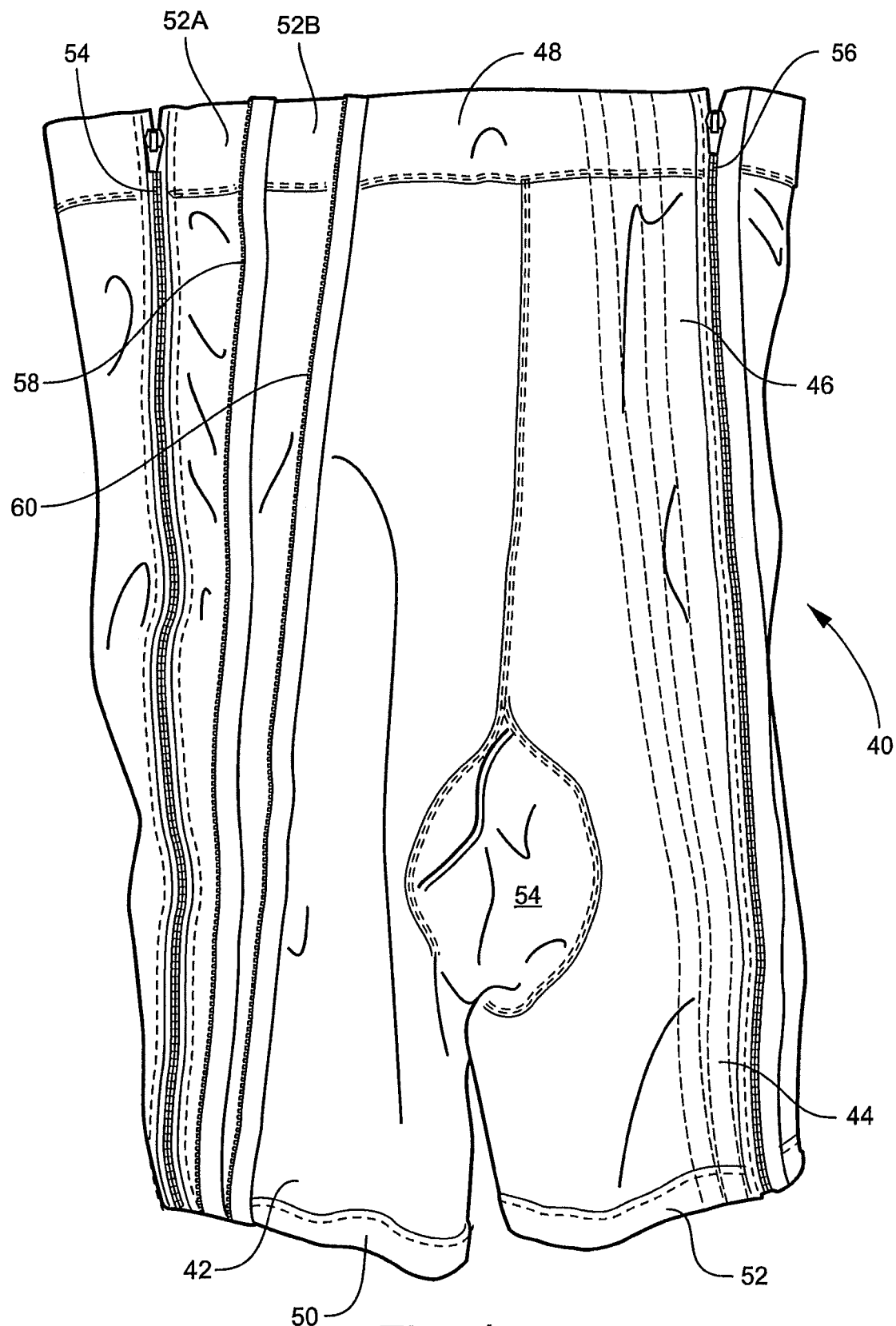
FIG. 4 illustrates another embodiment of a body an adjustable orthostatic_intolerance garment according to one embodiment of the invention.

Referring now to FIG. 4, the garment 40 is formed of a knitted spandex powernet construction using either 840 or 1120 Denier spandex yarns in order to provide pressure of about 55 mm Hg. when in place on the leg. The garment 40 includes legs 42, 44, and a torso portion 46 that extends upwardly into the abdominal area below the pectoral muscles. The garment 40 includes an elastic band 48 at the upper end and elastic bands 50, 52 at each leg bottom to prevent the legs 42, 44 from riding up the thigh. A fly for a male wearer or a flap (not shown) for use when worn by a female, is provided. In the particular embodiment shown in FIG. 4 legs 42, 44 include respective pairs of elongate tapered panels. Panels 52A, 52B, on the right side of the garment 40 is shown in FIG. 4. Identical panels are present, but not shown, on the left side of the garment 40. Zippers 54 and 56 extend the entire length of the garment 40 from the top to the bottom along the distal aspect of the thighs. Each side of the garment 40 may include a pair of additional zipper elements, such as zipper elements 58, 60 shown in the right side of the garment 40, or all of the size adjustment may be obtained by adjustments of the right side of the garment 40.

When initially donned by a wearer suffering from fluid loss, the garment 40 is used with the zipper 54 connected to the proximal zipper element 60, substantially as shown on the right side of the garment 40. As fluid is replaced in the wearer, the wearer may be given additional room with essentially the same or similar compression gradient by attaching the zipper 54 to the zipper element 58, and finally to position shown in FIG. 4. As noted above, all of the adjustment may be carried out with zipper 54, or a like adjustment may be made on the left hand side as well.

Figure 5:
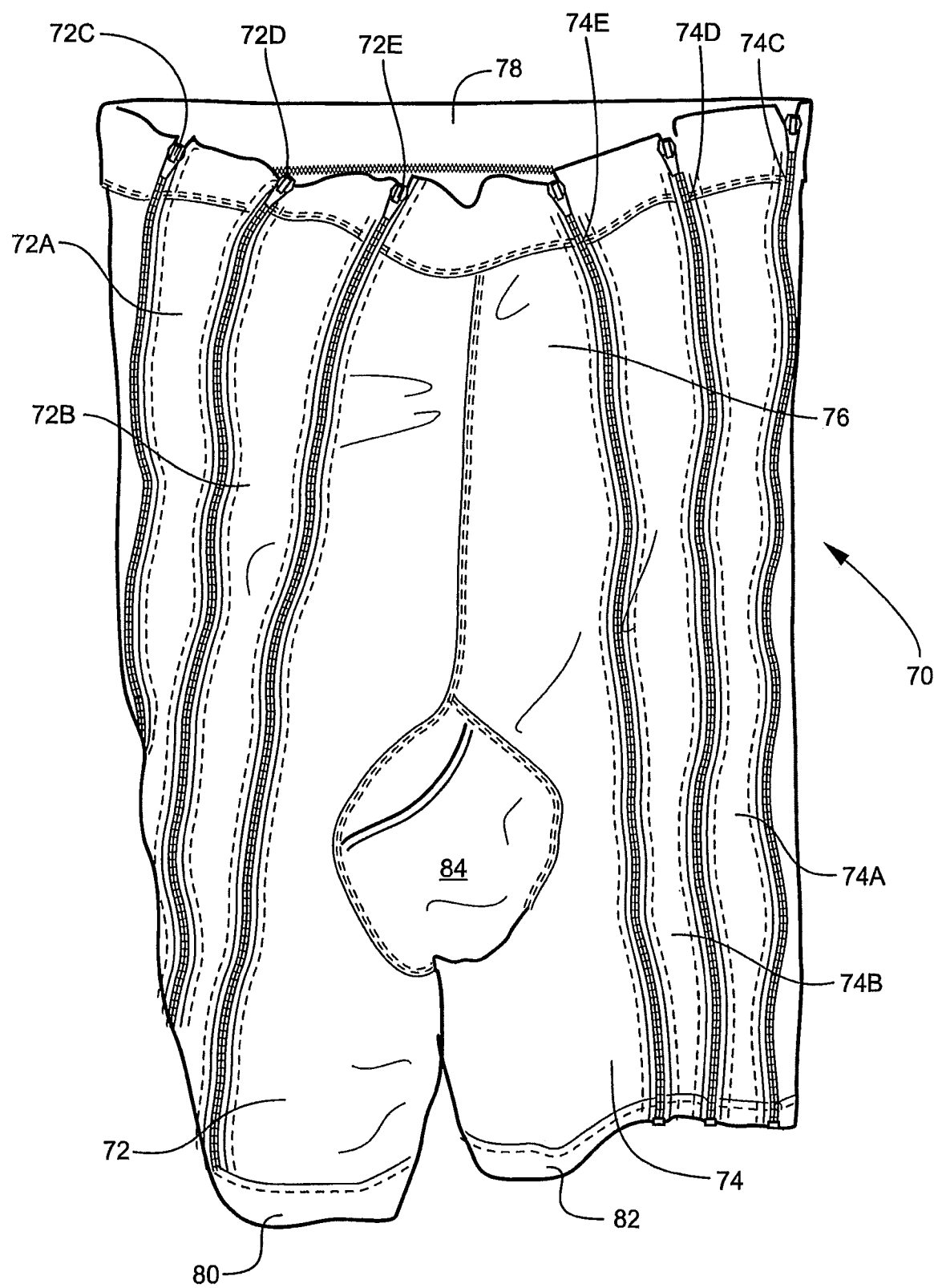
FIG. 5 illustrates another embodiment of a body an adjustable orthostatic_intolerance garment according to one embodiment of the invention.

Referring now to FIG. 5, the garment 70 is formed of a knitted spandex powernet construction using either 840 or 1120 Denier spandex yarns in order to provide pressure of about 55 mm Hg. when in place on the leg. The garment 70 includes legs 72, 74, and a torso portion 76 that extends upwardly into the abdominal area below the pectoral muscles. The garment 70 includes an elastic band 78 at the upper end and elastic bands 80, 82 at each leg bottom to prevent the legs 72, 74 from riding up the thigh. A fly 84 for male use or a flap (not shown) for use when worn by a female, is provided. In the particular embodiment shown in FIG. 5, legs 72, 74 each include a respective pair of elongate tapered panels 72A, 72B, 74A, 74B, that are retained in place by zippers 72C, D and E, and 74C, D and E.

When initially donned by a wearer suffering from fluid loss, the garment 70 is used without the panels 72A, 72B, 74A, 74B and the zippers 72C and 72E, and 74C and 74E are zipped together. As fluid is replaced in the wearer, the wearer may be given additional room with essentially the same or similar compression gradient by inserting the panels 72A and 74A into the garment 70. This is accomplished by unzipping the zippers and attaching the panels 72A, 74A to the garment 70 with the complementary zipper components, as shown. Finally, the panels 72B and 74B may likewise be inserted, in the same manner as described above.

Figure 6:
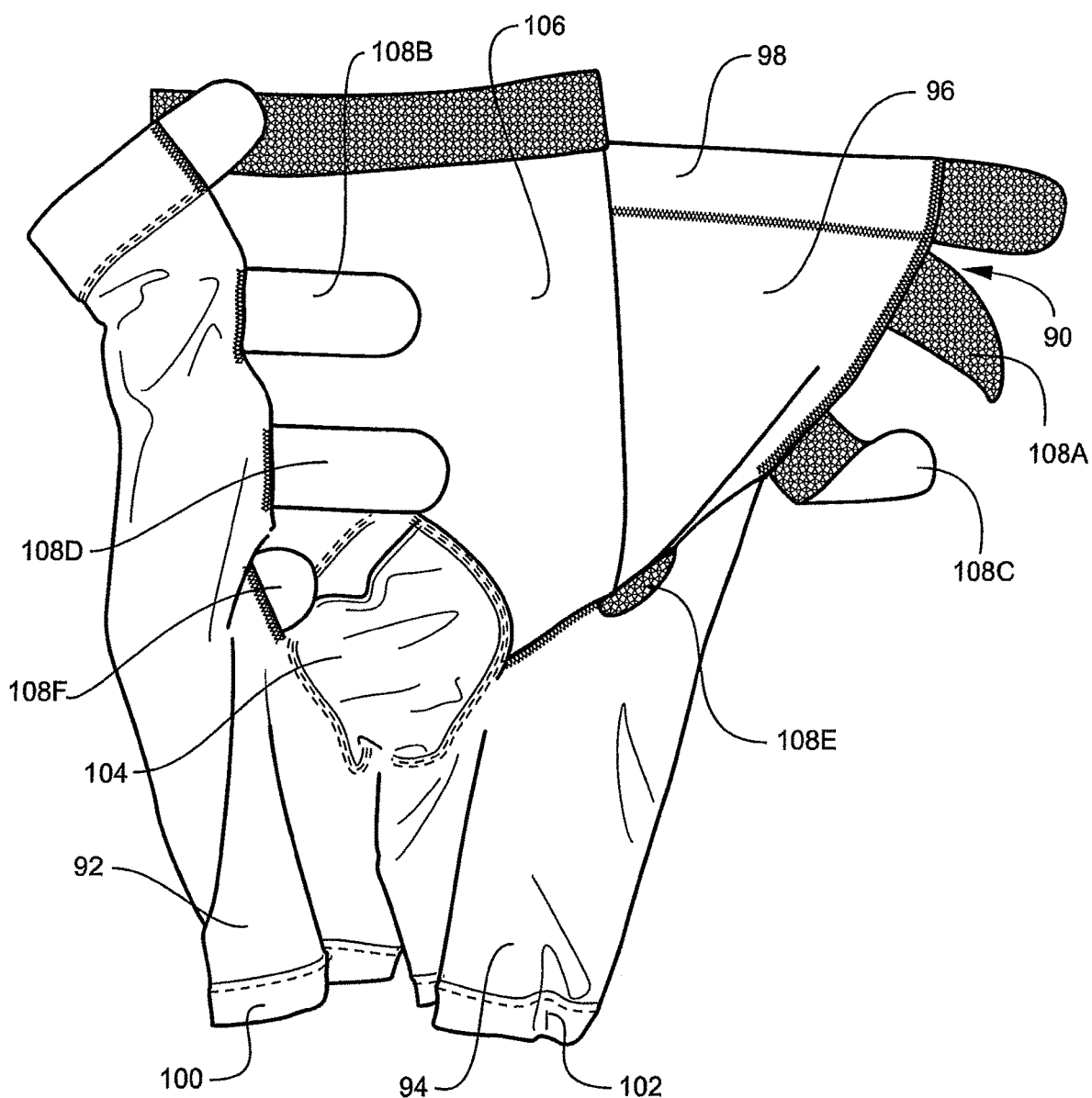
FIGS. 6 and 7 illustrate yet another embodiment of a body an adjustable_orthostatic intolerance garment according to one embodiment of the invention.
Figure 7:
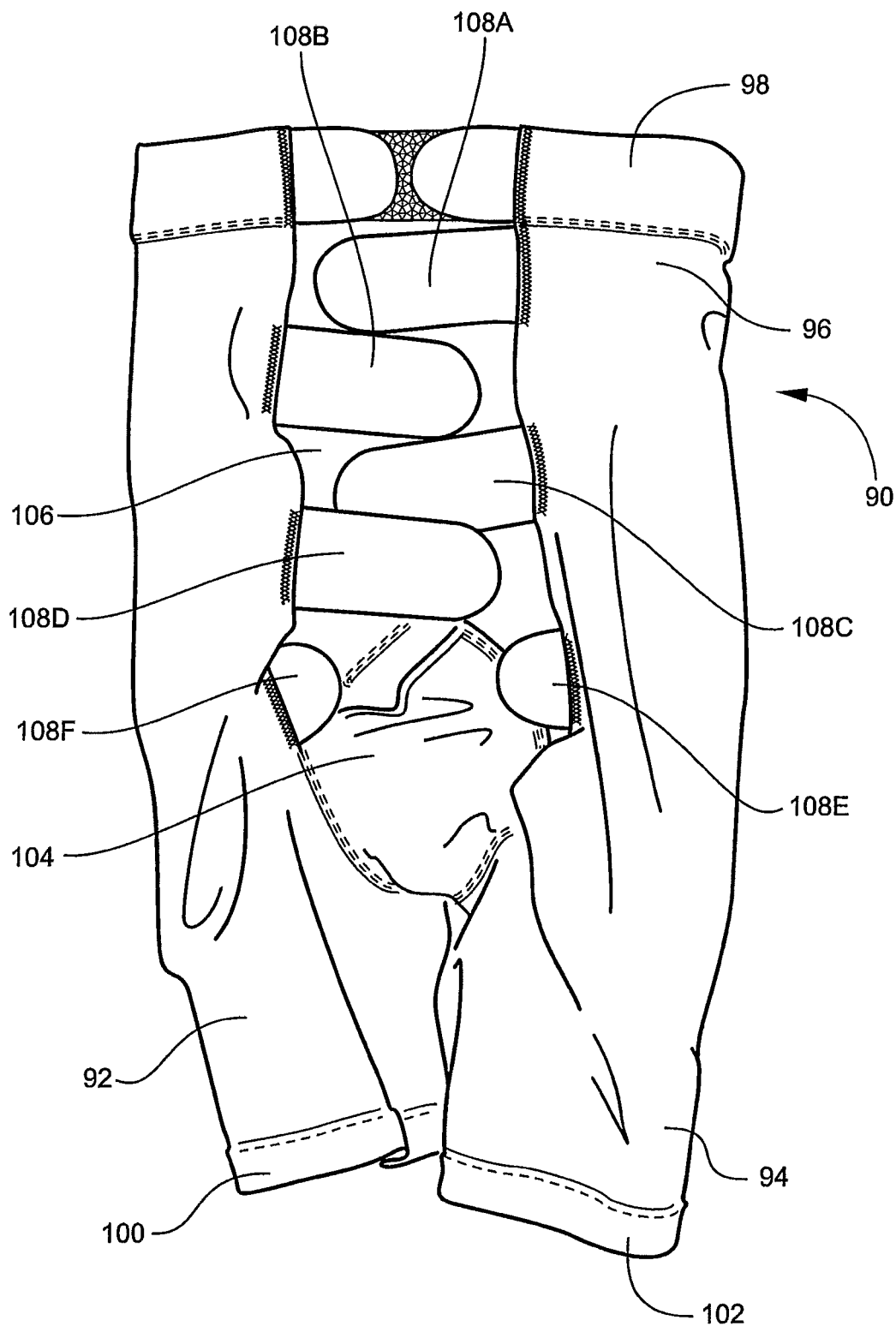

Referring now to FIGS. 6 and 7, another embodiment of an adjustable orthostatic intolerance garment is shown at reference numeral 90 that is formed of a knitted spandex powernet construction using either 840 or 1120 Denier spandex yarns in order to provide pressure of about 55 mm Hg. when in place on the leg. The garment 90 includes legs 92, 94 and a torso portion 96 that extends upwardly into the abdominal area below the pectoral muscles. The garment 90 includes an elastic band 98 at the upper end and elastic bands 100, 102 at each leg bottom to prevent the legs 92, 94 from riding up the thigh. A fly 104 for a male wearer or a flap (not shown) for use when worn by a female, is provided. In the particular embodiment shown in FIG. 6, the garment 90 includes a central panel 106 of a inelastic material having a fibrous surface adapted for being releasably engaged with complementary hooks of a conventional hook and loop system. The panel 106 is attached by stitching to the garment 90 on the bottom edge in the area of the fly 104, but is not attached on either side, and is freely moveable side-to-side as necessary for adjustment. The garment 90 includes opposing sets of adjustment straps 108 A-F that extend inwardly from opposing distal sides of the garment 90. The inward sides of the straps 108A-F are covered with hook-type touch fasteners that grip the fibrous surface of the panel 106 when pressed onto its surface. Thus, adjustment takes place by determining the correct compression to be applied to the wearer with the adjustment straps 108A-F in a released condition, and then pressing the straps 108A-F against the panel 106 to fix the compression at the desired level. The correct position of the straps 108A-F may be determined by markings applied to the garment indicating the approximate location of the straps 108A-F on the panel 106, or by other means.

With each of the embodiments described in this application, various methods of adjusting the compression of the garments may be used. For example, hook and loop systems, hook and eye systems, and criss-cross lacing systems (i.e., such as BOA devices with an adjustment knob that is turned for loosening or tightening the laces) may be used in lieu of and/or in combination with zippers.

Figure 8:
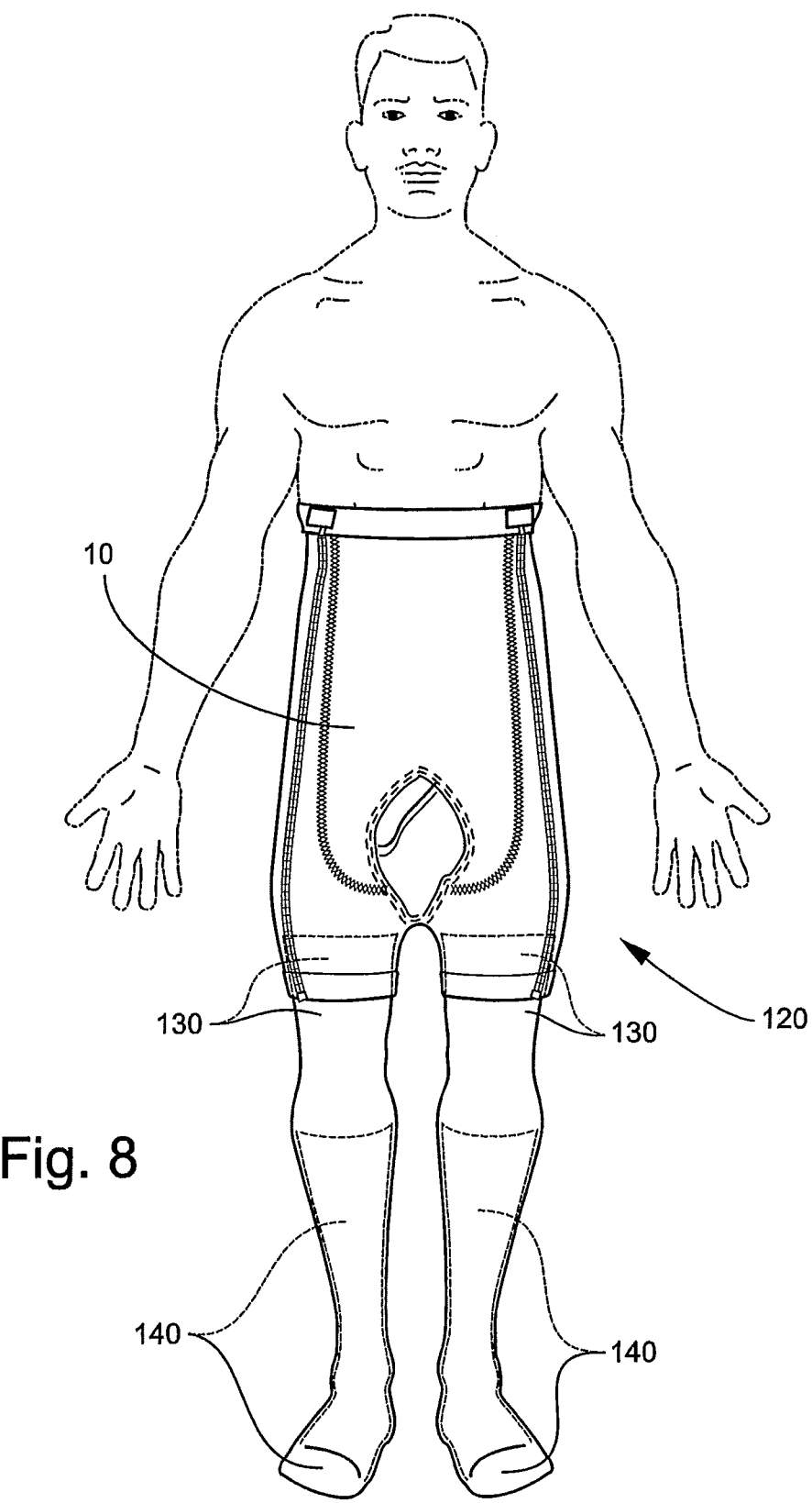
FIG. 8 illustrates an embodiment that incorporates with an adjustable_orthostatic intolerance garment according to one embodiment of the invention other_compression elements on the legs and feet of the wearer to form an adjustable-_orthostatic intolerance system.

Referring now to FIG. 8, an adjustable orthostatic intolerance garment according to one embodiment of the invention is combined with other compression elements on the legs and feet of the wearer to form an adjustable orthostatic intolerance system 120. For purposes of illustration, the garment 10 described above is shown, it being understood that any of the garments described in this application, whether or not illustrated, can be used as part of the system 120. Compression stockings 130 are worn In combination with the garment 10 to provide additional compression on the leg, and to prevent the garment 10 from causing pooling of fluids in the lower extremity. The basic construction of the compression stockings 130 is similar to that of the garment 10, i.e., a powernet construction of knitted spandex yarns of a predetermined suitable denier, as described above, or another suitable denier. As shown, the compression stockings 130 extend from the foot, have an open toe, and terminate on the upper thighs of the wearer a few inches above the bottom of the legs of the garment 10 so that there is an overlap of several inches on the legs.

Optionally, a liner sock 140 can be worn under the compression stockings 130. The liner socks 140 are preferably knitted of nylon, silk, or a combination of these or other flat yarns, and provide a low-friction surface to aid in donning the compression stockings 130. The liner socks 140 may also be treated with anti-microbial agents to reduce odor. Typically, the liner socks would extend upwardly to the calves of the wearer, as shown in FIG. 8, but may be either longer or shorter.

An adjustable orthostatic intolerance garment and garment system is described above. Various details of the invention may be changed without departing from the scope of the invention. Furthermore, the foregoing description of the preferred embodiment of the invention and best mode for practicing the invention are provided for the purpose of illustration only and not for the purpose of limitation, the invention being defined by the claims.

What is claimed is:

1. An adjustable orthostatic intolerance system comprising:
    an adjustable orthostatic intolerance garment, a left leg stocking and a right leg stocking, the garment comprising:
        a left leg portion and a right leg portion, each of the left and right leg portions having an elastic band fixed at a bottom thereof;
        a torso portion connected to and extending upwardly above the left leg portion and the right leg portion, wherein the torso portion is configured to be positioned at an abdominal area of a wearer below pectoral muscles of the wearer;
    a central panel attached to the torso portion via stitching at a bottom portion of the central panel and having a plurality of markings disposed on an outer surface of the central panel, the outer surface formed from an inelastic material having a fibrous surface; and
    a plurality of opposing sets of adjustment straps attached to distal sides of the torso portion, wherein each adjustment strap extends separately from another adjustment strap and inwardly from distal sides of the torso portion;
    wherein each one of the plurality of opposing sets of adjustment straps further comprises a plurality of hook type fasteners which releasably engage with the fibrous surface of the inelastic material of the outer surface of the central panel; and
    wherein each of the left leg stocking and the right leg stocking have an upper thigh-high proximal end terminating above the bottom of the respective left and right leg portions; and
wherein a combination of the adjustable orthostatic intolerance garment, the left leg stocking, and the right leg stocking maintains a gradient compression profile.

2. The adjustable orthostatic intolerance system of claim 1 wherein each of the left leg stockings and the right leg stockings have an open-toed distal end.

3. The adjustable orthostatic intolerance system garment of claim 2 where a compression profile of the left leg stocking and the right leg stocking includes a non-standard compression profile.

4. The adjustable orthostatic intolerance system of claim 3 wherein the non-standard compression profile of the left leg stocking and the right leg stocking includes a pressure of 55 mmHg at an ankle of a wearer and a pressure of 23 mmHg at a thigh of the wearer.

5. The adjustable orthostatic intolerance system of claim 4 wherein the non-standard compression profile of the left leg stocking and the right leg stocking is configured for maintaining a desired compression profile in a zero gravity environment and for countering the effects of orthostatic intolerance upon a wearer's return to earth's gravitational force.

6. The adjustable orthostatic intolerance system of claim 2 wherein the left leg portion, the right leg portion, the torso portion, the left leg stocking, and the right leg stocking each comprise a knitted compression fabric.

7. The adjustable orthostatic intolerance system of claim 6 wherein the knitted compression fabric is a spandex powernet construction using 840-1120 Denier spandex yarns.

8. The adjustable orthostatic intolerance system of claim 1 wherein the plurality of markings of the central panel correspond with a plurality of predetermined positions for releasably engaging the hook type fasteners of the plurality of opposing sets of adjustment straps with the fibrous surface of the inelastic material of the outer surface of the central panel.

9. The adjustable orthostatic intolerance system of claim 8 wherein the plurality of predetermined positions correspond to a plurality of correct compression levels.

10. The adjustable orthostatic intolerance system of claim 1 wherein the central panel is not attached to either side of the torso portion.

11. The adjustable orthostatic intolerance system of claim 1 wherein the torso portion comprises a dual layer of compression fabric.

12. An adjustable orthostatic intolerance system comprising:
an adjustable orthostatic intolerance garment, a left leg stocking and a right leg stocking, wherein the adjustable orthostatic intolerance garment comprises:
a left leg portion;
a right leg portion; and
a torso portion extending upwardly above the left leg portion and the right leg portion;
a central panel attached at a bottom portion to the torso portion and having a plurality of markings disposed on an outer surface, wherein the central panel is formed from a material having a fibrous surface; and
a plurality of adjustment straps fixedly attached to the torso portion and releasably attached via hook-type fasteners that grip the fibrous surface of the central panel when pressed onto the fibrous surface,
wherein each of the left leg stocking and the right leg stocking have an upper thigh-high proximal end terminating above a bottom of the respective left and right leg portions; and
wherein a combination of the adjustable orthostatic intolerance garment, the left leg stocking, and the right leg stocking maintains a gradient compression profile.

13. The adjustable orthostatic intolerance system of claim 12 wherein each of the left leg stocking and the right leg stocking have an open-toed distal end.

14. The adjustable orthostatic intolerance system of claim 13 wherein the left leg portion, the right leg portion, the torso portion, the left leg stocking, and the right leg stocking each comprise a knitted compression fabric.

15. The adjustable orthostatic intolerance system of claim 14 wherein the gradient compression profile of the left leg stocking and the right leg stocking includes a non-standard compression profile.

16. The adjustable orthostatic intolerance system of claim 15 wherein the non-standard compression profile is a pressure of 55 mmHg at an ankle of a wearer and a pressure of 23 mmHG at a thigh of the wearer.

17. The adjustable orthostatic intolerance system of claim 16 wherein the non-standard compression profile is configured for maintaining a desired compression profile in a zero gravity environment and for countering the effects of orthostatic intolerance upon a wearer's return to earth's gravitational force.

18. The adjustable orthostatic intolerance system of claim 14 wherein the knitted compression fabric is a spandex powernet construction using 840-1120 Denier spandex yarns.

19. The adjustable orthostatic intolerance system of claim 12 wherein the plurality of markings of the outer surface of the central panel correspond to a plurality of predetermined positions for the hook-type fasteners of the plurality of adjustment straps to attach to the central panel.

20. The adjustable orthostatic intolerance system of claim 19 wherein the plurality of predetermined positions correspond to a plurality of correct compression levels.

21. The adjustable orthostatic intolerance system of claim 12 wherein the torso portion comprises a dual layer compression fabric.

22. The adjustable orthostatic intolerance system of claim 12, wherein the central panel comprises an inelastic material.

* * * * *